United States Patent
Kang et al.

(10) Patent No.: US 12,064,441 B2
(45) Date of Patent: Aug. 20, 2024

(54) COMPOSITION FOR PREVENTING OR TREATING KELOID

(71) Applicants: CHUNGNAM NATIONAL UNIVERSITY HOSPITAL, Daejeon (KR); THE INDUSTRY & ACADEMIC COOPERATION IN CHUNGNAM NATIONAL UNIVERSITY (IAC), Daejeon (KR)

(72) Inventors: Yea Eun Kang, Daejeon (KR); Sang-Ha Oh, Daejeon (KR); Sunje Kim, Daejeon (KR); Seong Eun Lee, Daejeon (KR); Shinae Yi, Daejeon (KR); Mi Ae Lim, Daejeon (KR)

(73) Assignees: CHUNGNAM NATIONAL UNIVERSITY HOSPITAL, Daejeon (KR); THE INDUSTRY & ACADEMIC COOPERATION IN CHUNGNAM NATIONAL UNIVERSITY (IAC), Daejeon (KR)

( * ) Notice: Subject to any disclaimer, the term of this patent is extended or adjusted under 35 U.S.C. 154(b) by 0 days.

(21) Appl. No.: 17/818,378

(22) Filed: Aug. 9, 2022

(65) Prior Publication Data
US 2023/0046998 A1     Feb. 16, 2023

(30) Foreign Application Priority Data
Aug. 10, 2021   (KR) ........................ 10-2021-0105047

(51) Int. Cl.
  A61K 31/575   (2006.01)
  A61K 8/46     (2006.01)
  A61K 9/00     (2006.01)
  A61K 9/06     (2006.01)
  A61P 17/02    (2006.01)

(52) U.S. Cl.
  CPC ............ *A61K 31/575* (2013.01); *A61K 8/466* (2013.01); *A61K 9/0021* (2013.01); *A61K 9/06* (2013.01); *A61P 17/02* (2018.01)

(58) Field of Classification Search
  CPC .................................................. A61K 31/575
  See application file for complete search history.

(56) References Cited

FOREIGN PATENT DOCUMENTS

| KR | 10-2003-0003952 A | 1/2003 |
| KR | 10-1112051 B1 | 2/2012 |
| KR | 10-1505294 B1 | 3/2015 |
| KR | 10-2018-0036580 A | 4/2018 |
| KR | 10-2039217 B1 | 10/2019 |

OTHER PUBLICATIONS

Bartlett "Exploiting Chemical Diversity for Drug Discovery" Edited by Paul A Bartlett and Michael Entzeroth, The Royal Society of Chemistry, 2006, pp. 113-118.*
"Find ETDs Home » Thesis Resources » Find ETDs" Online: "https://ndltd.org/thesis-resources/find-etds/" Accessed Jan. 31, 2023.*
Irwin "ZINC—A Free Database of Commercially Available Compounds for Virtual Screening" J. Chem. Inf. Model. 2005, 45, 177-182.*
Kim "PubChem in 2021: new data content and improved web interfaces" Nucleic Acids Research, 2021, vol. 49, Database issue Published online Nov. 5, 2020.*
STN REGISTRY/ZREGISTRY (CAS REGISTRYSM) Sep. 2016 2 pages.*
Kim, International Journal of Molecular Sciences (2021),22(19), 10765.*
Yamaguchi, Journal of Dermatological Science (1998), 18(1), 35-42.*
Betarbet, Journal of Clinical and Aesthetic Dermatology, 13(2), 2020, 33-43.*
Kim et al., "Tauroursodeoxycholic Acid Decreases Keloid Formation by Reducing Endoplasmic Reticulum Stress as Implicated in the Pathogenesis of Keloid", Int. J. Mol. Sci., 2021, 22, 10765, 15 pages.
Yuan et al., "Low-grade inflammatory polarization of monocytes impairs wound healing", J Pathol 2016, 238: 571-583.

\* cited by examiner

*Primary Examiner* — Nizal S Chandrakumar
(74) *Attorney, Agent, or Firm* — Vorys, Sater, Seymour and Pease LLP; Mih Suhn Koh

(57) ABSTRACT

Provided are a composition for treating or preventing recurrence of keloid comprising tauroursodeoxycholic acid as an active ingredient, and a method for treating keloid or preventing recurrence of keloid using the composition.

5 Claims, 11 Drawing Sheets

| Patient | Group | Age(y)/Sex | Site | Operation |
|---|---|---|---|---|
| 1 | control | 42/F | Back | Soft tissue Mass excision |
| 2 | control | 43/F | Chest | Soft tissue Mass excision |
| 3 | control | 28/F | cheek | Soft tissue Mass excision |
| 4 | control | 67/F | Neck | Neck lift surgery |
| 5 | keloid | 28/F | Ear | Keloid Scar revision |
| 6 | keloid | 23/F | Ear | Keloid Scar revision |
| 7 | keloid | 46/F | Abdomen | Keloid Scar revision |
| 8 | keloid | 29/F | Ear | Keloid Scar revision |
| 9 | keloid | 57/F | Ear | Keloid Scar revision |

COMPOSITION FOR PREVENTING OR TREATING KELOID

BACKGROUND

Technical Field

The present invention relates to a composition for preventing or treating keloids comprising tauroursodeoxycholic acid.

Background Art

Keloid is a pathological skin condition in which excessive collagen is accumulated in the dermis and subcutaneous fat layer by various external stimuli such as trauma, burns, infection, injection and surgery. There is a large difference in the incidence rate by race, and family history and location are presumed to be important causes, but the exact mechanism of its occurrence is still unknown. Unlike the general wound healing process, keloid is a disease in which the scars grow larger and swell beyond the wound site as the skin's wound regeneration process is abnormally performed. The most commonly used form of conventional keloid treatment is intradermal steroid injections. However, after intradermal injection of steroids, local side effects such as skin depression, pigment changes, and vasodilation are common, and even if it is a local injection, since it is a hormonal product, side effects of systemic hormones such as amenorrhea, changes in the menstrual cycle, and hypoadrenocorticism may appear. As for the local side effects after steroid injection, as shown in previous studies, the inhibitory effect of steroids on fibroblasts is not significantly different between normal fibroblasts and keloid fibroblasts, it may even cause atrophy of normal cells around keloids in actual clinical application.

Korean Patent No. 1505294 relates to a composition for reducing keloid or scar formation and discloses a pharmaceutical composition for reducing keloid or scar formation comprising a starfish hatching liquid extract as an active ingredient, and Korea Patent No. 1112051 relates to a composition for preventing or treating hypertrophic scars or keloids and discloses a composition containing α-NeuNAc-(2→3)-β-D-Gal-(1→4)-D-Glc or α-NeuNAc-(2→6)-β-D-Gal-(1→4)-D-Glc sialyllactose, and Korea Patent No. 2039217 relates to a non-thermal atmospheric pressure plasma keloid treatment device and its use and discloses a pharmaceutical composition for preventing or treating keloids using plasma, but there is no disclosure regarding the composition for preventing or treating keloids comprising tauroursodeoxycholic acid of the present invention.

Also, tauroursodeoxycholic acid has been proven to be effective in hyperfibroproliferative diseases such as hepatobiliary sclerosis and pulmonary fibrosis. However, there has been no report on the treatment of keloids using tauroursodeoxycholic acid.

DETAILED DESCRIPTION OF THE INVENTION

Summary

The present invention has been derived from the above needs, and the present inventors have completed the present invention by confirming that tauroursodeoxycholic acid is effective in keloid fibroblasts compared to normal fibroblasts in human tissue-derived fibroblasts and keloid tissue-derived fibroblasts as a single treatment regimen for keloid lesions.

Technical Solution

In order to solve the above problem, the present invention provides a pharmaceutical composition for keloid treatment or recurrence prevention comprising tauroursodeoxycholic acid as an active ingredient.

In one embodiment of the present invention, the tauroursodeoxycholic acid may be injected into the dermis.

In another example of the present invention, the composition comprises an additional component or method effective for the treatment of keloids or scars, wherein the additional component or method may include one or more selected from the group consisting of an anti-inflammatory agent, an anti-fibrotic agent, a laser, and surgery.

In another example of the present invention, the composition may be in the form of an external preparation for skin or an injection.

Also, the present invention provides a cosmetic composition for improving or preventing recurrence of keloid comprising tauroursodeoxycholic acid as an active ingredient.

The present invention provides a kit for improving or preventing recurrence of keloids comprising the composition and instructions for use.

Additionally, the present invention provides a method for improving or preventing recurrence of keloids in animals other than humans, comprising the step of administering tauroursodeoxycholic acid.

Effects of the Invention

The present invention relates to a composition for preventing or treating keloids comprising tauroursodeoxycholic acid as an active ingredient. For the first time, by studying the effect of direct intralesional injection of tauroursodeoxycholic acid solution, since excellent results have been confirmed compared to the control and comparative groups, which are steroid injections, it can be usefully used as a new keloid treatment that can replace the existing steroid treatment.

DETAILED DESCRIPTION

Hereinafter, preferred embodiments of the present invention will be described in detail. In addition, in the following description, many specific details such as specific components are shown, it will be apparent to those of ordinary skill in the art that the present invention may be practiced without these specific details only provided to help a more general understanding of the present invention. And, in describing the present invention, if it is determined that a detailed description of a related known function or configuration may unnecessarily obscure the gist of the present invention, the detailed description thereof will be omitted.

As used herein, the term "treatment" means to stop the progression of damage by suppressing the progression and/or exacerbation of symptoms even if not completely cured, or to ameliorate some or all of the symptoms to guide them in the direction of healing.

In the present invention, the term "improvement" refers to any action in which symptoms are improved or beneficially changed.

In order to achieve the object of the present invention, the present invention provides a pharmaceutical composition for keloid treatment or recurrence prevention comprising tauroursodeoxycholic acid as an active ingredient.

In one embodiment of the present invention, the tauroursodeoxycholic acid may be injected into the dermis.

In another embodiment of the present invention, the composition comprises an additional component or method effective for the treatment of keloids or scars, wherein the additional component or method may include one or more selected from the group consisting of an anti-inflammatory agent, an anti-fibrotic agent, a laser, and surgery.

In another example of the present invention, the composition may be in the form of an external preparation for skin or an injection.

The composition of the present invention may be prepared in any form of composition, further including suitable carriers, excipients and diluents commonly used in the preparation of the composition and may preferably be prepared in the form of a pharmaceutical composition, a health functional food composition or a cosmetic composition, but is not limited thereto.

The pharmaceutical composition of the present invention, according to conventional methods, may be formulated in the form of oral dosage forms such as powders, granules, tablets, capsules, suspensions, emulsions, syrups, aerosols, and of external preparations, suppositories and sterile injection solutions, and powders, tablets, capsules, injections and liquids are more preferred. Such formulation may be carried out by a method conventionally performed in the pharmaceutical field, and using the method disclosed in Remington's Pharmaceutical Science, Mack Publishing Company, Easton PA, the formulation can be preferably formulated according to each disease or component.

Carriers, excipients and diluents that may be included in the pharmaceutical composition include lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinylpyrrolidone, water, methylhydroxybenzoate, propylhydroxybenzoate, talc, magnesium stearate, and mineral oil.

In the case of formulation, it may be prepared by additionally using diluents or excipients such as commonly used fillers, extenders, binders, wetting agents, disintegrants, and surfactants.

Solid preparations for oral administration include tablets, pills, powders, granules, capsules, and the like, and such solid preparations include at least one excipient, for example, starch, calcium carbonate, sucrose or lactose, gelatin, etc. In addition to simple excipients, lubricants such as magnesium stearate and talc are also used.

Liquid formulations for oral administration include suspensions, oral solutions, emulsions, syrups, etc. In addition to water and liquid paraffin, which are commonly used simple diluents, various excipients, for example, wetting agents, sweetening agents, fragrances, preservatives, and the like may be included. Formulations for parenteral administration include sterile aqueous solutions, non-aqueous solutions, suspensions, emulsions, freeze-dried preparations, and suppositories. As the non-aqueous agent and suspending agent, propylene glycol, polyethylene glycol, vegetable oils such as olive oil, and injectable esters such as ethyl oleate may be used. As the base of the suppository, witepsol, macrogol, tween, cacao butter, laurin butter, glycerogelatin, and the like can be used.

The preparation may be a solid preparation such as a powder or granule, but from the viewpoint of obtaining a more excellent keloid treatment effect, a solution for injection such as a solution, an emulsion, a suspension, or a gel for injection may be used. As a manufacturing method of the liquid formulation mentioned above, for example, the method of mixing TUDCA with a solvent, and the method of mixing a suspending agent and an emulsifier can be illustrated suitably, and as a method for producing the above-mentioned gel, for example, a method of mixing TUDCA with gelatin can be appropriately exemplified. As described above, in the case of using TUDCA as a formulation in the present invention, depending on the needs of the formulation, optional ingredients such as an appropriate pharmaceutically acceptable carrier, for example, excipients, binders, solvents, solubilizers, suspending agents, emulsifiers, isotonic agents, buffers, stabilizers, soothing agents, preservatives, antioxidants, coloring agents, etc. may be formulated.

Examples of the above-described solvent include hydrophilic solvents such as purified water, physiological saline, Ringer's solution, ethanol, propylene glycol, glycerin, polyethylene glycol, and macrogol or oily solvents such as olive oil, peanut oil, sesame oil, camellia oil, rapeseed oil, fatty acid monoglycerides, fatty acid diglycerides, higher fatty acid esters, liquid paraffin, etc. can be exemplified. In addition, as the above-mentioned suspending agent, stearyl triethanolamine, sodium lauryl sulfate, lauryl aminopropionic acid, lecithin, benzalkonium chloride, benzethonium chloride, glycerin monostearate, polyvinyl alcohol, polyvinyl pyrrolidone, carboxymethyl cellulose sodium, methyl cellulose, hydroxymethyl cellulose, hydroxyethyl cellulose, hydroxypropyl cellulose, polysorbates, polyoxyethylene hydrogenated castor oil, gum arabic, bentonite, and the like can be exemplified, furthermore, examples of the above-mentioned emulsifiers include gum arabic, gelatin, lecithin, cholesterol, egg yolk, bentonite, veegum, cetanol, glycerin monostearate, methyl cellulose, sodium carboxymethyl cellulose, and stearic acid.

Examples of the above-described solubilizing agent include polyethylene glycol, propylene glycol, D-mannitol, trehalose, benzyl benzoate, ethanol, trisaminomethane, cholesterol, triethanolamine, sodium carbonate, sodium citrate, sodium salicylate, sodium acetate, and the like. Examples of the above-mentioned excipients include lactose, sucrose, D-sorbitol, starch, α-starch, corn starch, D-mannitol, dextrin, crystalline cellulose, gum arabic, low-substituted hydroxypropyl cellulose, sodium carboxymethylcellulose, methylcellulose, Serum albumin and the like can be exemplified. Moreover, as the above-mentioned binder, α-starch, sucrose, gelatin, gum arabic, methyl cellulose, carboxymethyl cellulose, sodium carboxymethyl cellulose, crystalline cellulose, sucrose, D-mannitol, trehalose, dextrin, pullulan, hydroxy propyl cellulose, hydroxy propyl methyl cellulose, polyvinyl pyrrolidone, polyvinyl alcohol, and the like can be exemplified.

Examples of the isotonic agent described above include sodium chloride, potassium chloride, glucose, fructose, mannitol, sorbitol, lactose, sucrose, glycerin, urea, and the like. In addition, as the above-mentioned buffer, sodium citrate, glycerin, etc. can be exemplified. Further, examples of the preservative include paraoxybenzoic acid esters, chlorobutanol, benzyl alcohol, phenethyl alcohol, dehydroacetic acid and sorbic acid. Examples of the above-described stabilizer include polyethylene glycol, sodium dextran sulfate, amino acids, human serum albumin, and the like. In addition, glucose, calcium gluconate, procaine hydrochloride, etc. can be exemplified as the above-described analgesic agent. Moreover, sulfite, ascorbic acid, etc. can be illustrated as an antioxidant mentioned above. In addition, as the above-mentioned colorant, tar-based pigment, caramel, bengala, titanium dioxide, FD&C dyes such as FD&C Blue No. 2 and FD&C Red No. 40 by Eris and Everald can be exemplified.

The preferred dosage of the composition of the present invention varies depending on the condition and weight of the patient, the degree of disease, the drug form, the route of administration, and the duration, but may be appropriately selected by those skilled in the art. However, for a desirable effect, the active ingredient of the present invention may be included in an amount of 0.01 to 99.9% by weight, preferably 0.1 to 99% by weight per day. The daily dose may be about 0.1~1,000 mg/kg, preferably 100~300 mg/kg.

In addition, the present invention provides a cosmetic composition for improving or preventing recurrence of keloid comprising tauroursodeoxycholic acid as an active ingredient.

The cosmetic composition of the present invention may have a formulation selected from the group consisting of an external skin ointment, cream, softening lotion, nourishing lotion, pack, essence, hair tonic, shampoo, conditioner, hair conditioner, hair treatment, gel, skin lotion, skin softener, skin toner, astringent, lotion, milk lotion, moisture lotion, nourishing lotion, massage cream, nourishing cream, moisture cream, hand cream, foundation, nourishing essence, sunscreen, soap, cleansing foam, cleansing lotion, cleansing cream, body lotion and body cleanser, but is not limited thereto. The composition of each of these dosage forms may contain various bases and additives necessary and appropriate for the formulation of the dosage form, and the types and amounts of these components can be easily selected by those skilled in the art.

When the formulation of the present invention is a paste, cream or gel, animal fiber, vegetable fiber, wax, paraffin, starch, tracanth, cellulose derivative, polyethylene glycol, silicone, bentonite, silica, talc or zinc oxide may be used as a carrier component.

When the formulation of the present invention is a powder or a spray, lactose, talc, silica, aluminum hydroxide, calcium silicate or polyamide powder may be used as a carrier component, and especially in the case of a spray, it may additionally contain a propellant such as chlorofluorohydrocarbon, propane/butane or dimethyl ether.

When the formulation of the present invention is a solution or emulsion, a solvent, solvating agent or emulsifying agent is used as a carrier component, examples are water, ethanol, isopropanol, ethyl carbonate, ethyl acetate, benzyl alcohol, benzyl benzoate, propyleneglycol, 1,3-butylglycol oil, glycerol aliphatic esters, fatty acid esters of polyethylene glycol or sorbitan.

When the formulation of the present invention is a suspension, as a carrier component, liquid diluents such as water, ethanol or propylene glycol, suspending agents such as ethoxylated isostearyl alcohol, polyoxyethylene sorbitol esters and polyoxyethylene sorbitan esters, microcrystalline cellulose, aluminum metahydroxide, bentonite, agar or tracanth, etc. may be used.

When the formulation of the present invention is a surfactant-containing cleansing, aliphatic alcohol sulfate, aliphatic alcohol ether sulfate, sulfosuccinic acid monoester, isethionate, imidazolinium derivative, methyl taurate, sarcosinate, fatty acid amide ether sulfate, alkylamidobetaine, aliphatic alcohol, fatty acid glycerides, fatty acid diethanolamides, vegetable oils, linolin derivatives, or ethoxylated glycerol fatty acid esters, etc. may be used as carrier component.

The formulation of the present invention may further contain excipients including fluorescent substances, fungicides, hydrotropes, moisturizers, fragrances, fragrance carriers, proteins, solubilizers, sugar derivatives, sunscreens, vitamins, plant extracts, and the like.

The present invention provides a kit for improving or preventing recurrence of keloids comprising the composition and instructions for use.

Additionally, the present invention provides a method for improving or preventing recurrence of keloids in animals other than humans, comprising the step of administering tauroursodeoxycholic acid.

Advantages and features of the present invention, and methods of achieving them, will become apparent with reference to the embodiments described below in detail. However, the present invention is not limited to the embodiments disclosed below, but will be implemented in various different forms, and only the present embodiments are provided so that the disclosure of the present invention is complete, and to completely inform those of ordinary skill in the art to which the present invention belongs, the scope of the invention, and the invention is only defined by the scope of the claims.

Example 1

1. Patient Group

From 2018 to 2019, clinical trials were approved for patients who visited the outpatient department of Plastic Surgery at Chungnam National University Hospital (IRB no. 2018-12-050), and a total of 3 normal controls and 9 keloid patients were recruited.

2. Western Blot Analysis

Tissues were homogenized using a TissueLyzer II (Qiagen, Hilden, Germany). Cells and tissues were lysed in RIPA buffer (30 mM Tris [pH 7.5], 150 mM sodium chloride, 1 mM sodium phenylmethylsulfonyl fluoride, 1 mM sodium orthovanadate, 1% Nonidet P-40, 10% glycerol, phosphatase and protease inhibitors). Western blot analysis was performed with 40 μg of protein using a commercially available antibody. Anti-CHOP, anti-pERK, anti-ERK, anti-IRE1α, anti-pIRE1α, anti-pSMAD2/3 and anti-β-actin antibodies were purchased from Cell Signaling Technology (Beverly, MA, USA). Anti-COL1A1, anti-ATF4, anti-TGFβ1, anti-IL-1 antibodies and secondary antibodies were purchased from Santa Cruz Biotechnology (Santa Cruz, CA, USA) was used. Immune response bands were visualized by enhanced chemiluminescence (ECL) (Bio-Rad, Hercules, CA, USA), and images were scanned using an Odyssey imaging system and quantified using Image Studio Digits (LI-COR Biosciences, Lincoln, NE, USA).

3. Transmission Electron Microscopy (TEM)

Tissue samples from keloid patients or rabbits were fixed in 1% glutaraldehyde at 4° C. and washed with 0.1M cacodylate buffer (pH 7.2) at 4° C. The washed sample was fixed with 0.1 M phosphate buffer containing 1% osmium tetroxide (0504) at 4° C. for 1 hour. The samples were dehydrated in ethanol solutions (50, 75, 90, 95 and 100%) and placed in propylene oxide. The dehydrated sample was embedded in Embed-912 resin (Electron Microscopy Sciences, Hatfield, PA, USA) and polymerized at 70° C. for 24 hours. Tissues were cut at 80 nm on a Leica ultramicrotome (Leica, Bensheim, Germany) using a diamond knife and the sectioned samples were stained with 4% uranyl acetate and citrate and observed at 120 kV using a Leo912 transmission electron microscope (Carl Zeiss, Oberkochen, Germany).

4. Cell Culture and Cell Experiments

Human keloid-derived fibroblasts and normal skin-derived fibroblasts were cultured in Dulbecco's modified Eagle's medium (DMEM; Invitrogen), 10% fetal bovine serum (FBS; Hyclone, Logan, UT, USA), 100 U/mL penicillin and 100 g/mL streptomycin (Invitrogen) media at 5% $CO_2$. Keloid-derived fibroblasts are placed $1\times10^4$/well on 96-well plates, after treatment with tauroursodeoxycholic acid (TUDCA; Merck Millipore, Billerica, MA, USA) for 24 hours, cell proliferation was measured with an enzyme-linked immunosorbent assay reader using a 450 nm WST-1 (Roche Diagnostics Corporation, Indianapolis, IN, USA) assay.

5. Keloid Rabbit Animal Experiments

Figure 1:
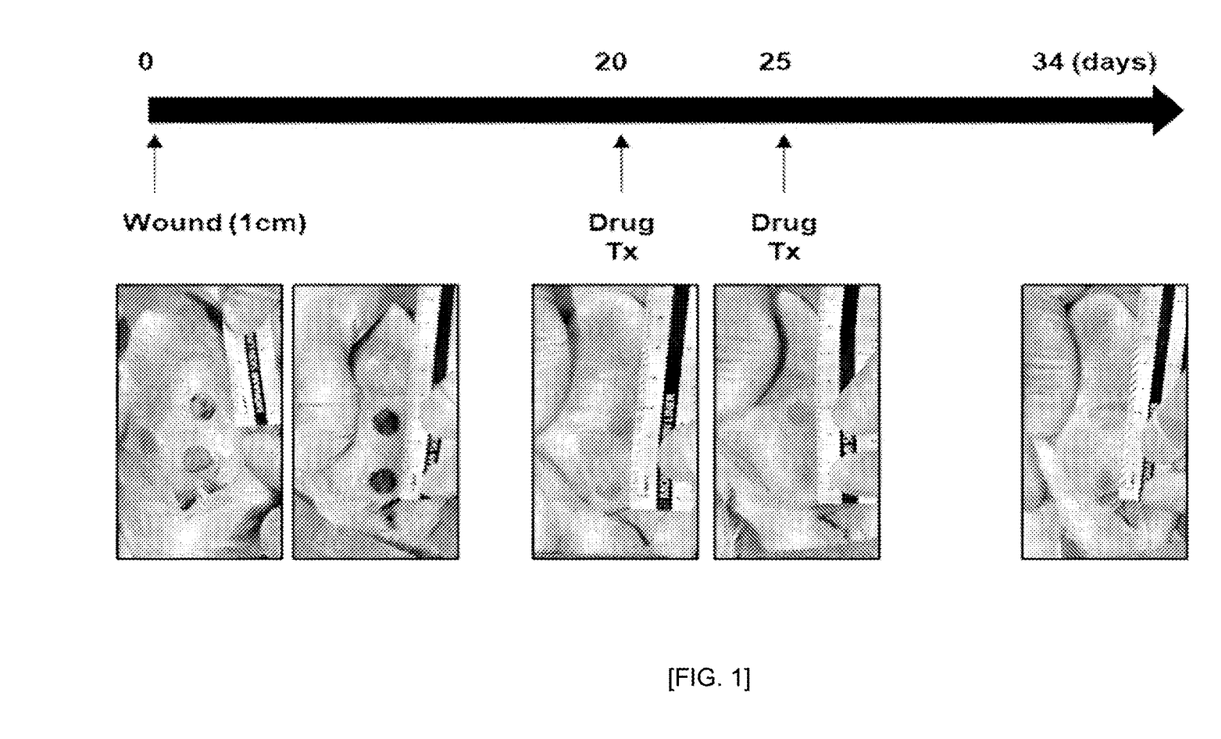
FIG. 1 shows a method for generating a rabbit model.

Animal studies were performed with the approval of the Preclinical Research Center (CNUH-019-A0079) of Chungnam National University Hospital. A 12-month-old female New Zealand white rabbit weighing about 4 kg was purchased from Damul Science (Daejeon, Korea), and all rabbits were kept individually in cages and received humane care according to institutional guidelines. After anesthetizing rabbits with a mixture of ketamine (60 mg/kg) and xylazine (5 mg/kg), the side ear hairs were shaved, disinfected with povidone-iodine, and then anesthetized. Next, after using a 10 mm biopsy punch to make 2 circular wounds with a diameter of 10 mm on the ventral surface of each ear, and covering the wound with an adhesive polyurethane dressing (Tegaderm; 3M, Minneapolis, MN, USA), and once a day, the wound areas were disinfected with physiological saline and observed, and the adhesive polyurethane dressing was replaced. After wound formation, a simple dressing was maintained for 20 days to form a thick scar tissue, and on days 20 and 25 after wounding, saline, steroid (10 mg/mL) or TUDCA (10 mg/mL) was administered to the dermal region of the rabbit ear scar using a 30-gauge syringe (FIG. 1).

Figure 2:
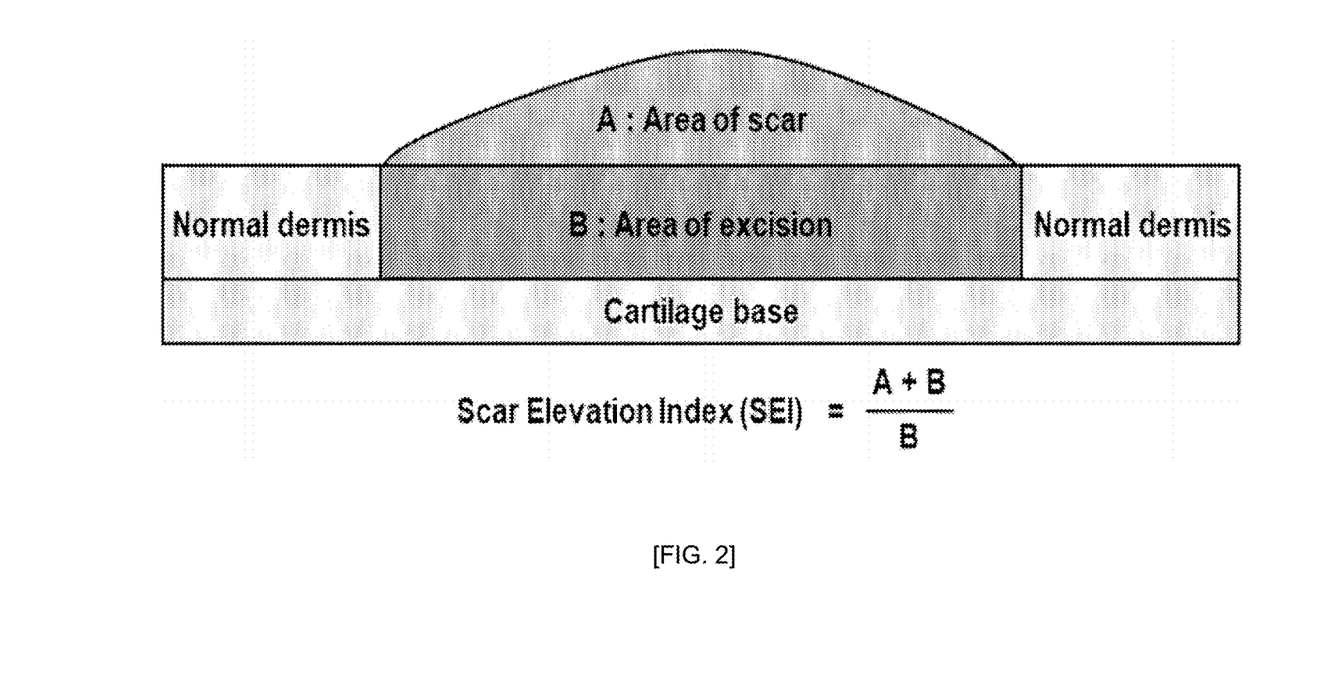
FIG. 2 shows a keloid evaluation method.

6. Scar Elevation Index (SEI) Calculation (Methods for Evaluating Keloid Tissue) SEI gives the ratio of total hypertrophic scar area to normal tissue present beneath the scar. In the present invention, the region where the cartilage layer is left as it is and the skin layer is excised is the B region. Area A contains an excessive amount of soft tissue compared to the surrounding normal dermal layer. An SEI greater than 1 indicates the formation of hypertrophic scars, keloids (FIG. 2).

Test Example

1. Clinical Aspects of the Patient

Figure 3:
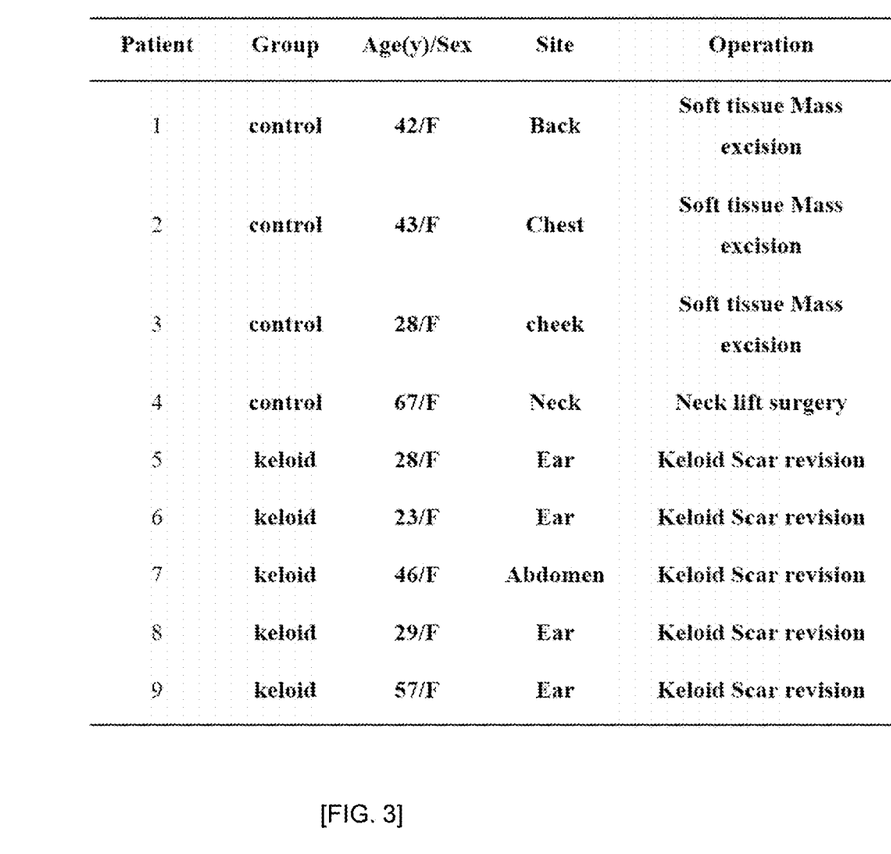
FIG. 3 shows the clinical aspects of the test subject patient.

The clinical picture of the patient is as shown in FIG. 3.

Figure 4A:
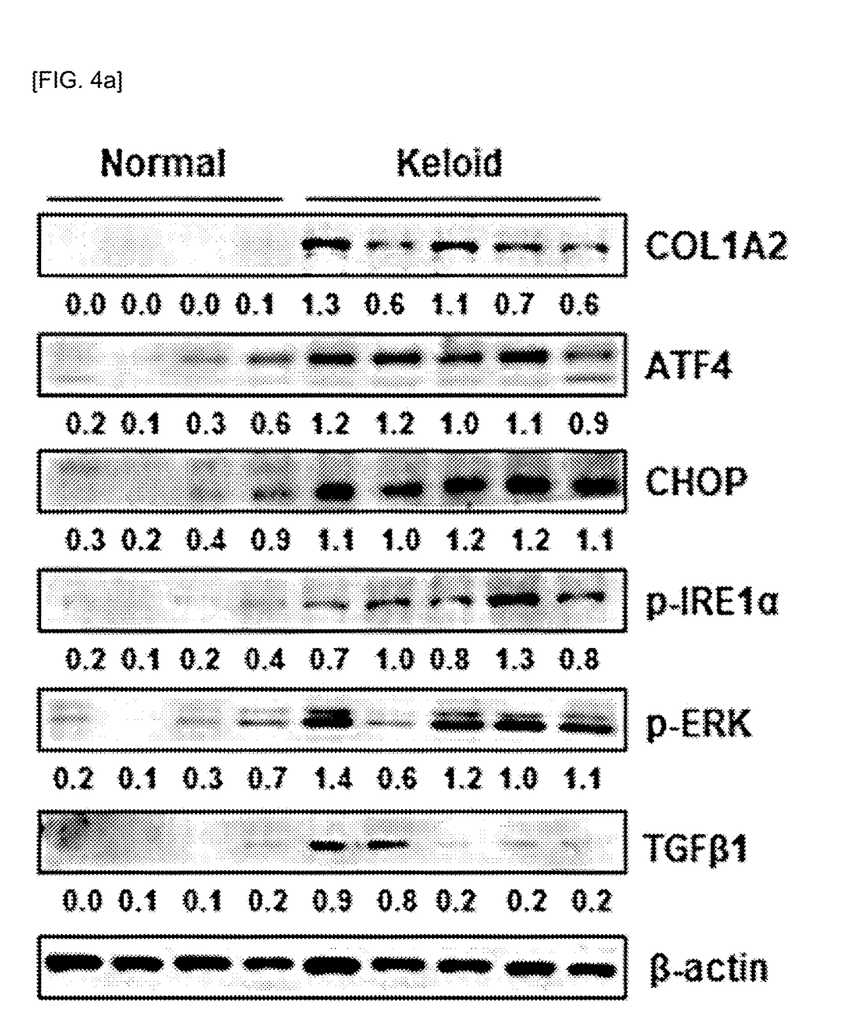
FIG. 4A-4B shows the increase in ER stress and changes in fibrosis markers in human keloid tissues compared to normal human tissues.
Figure 4B:
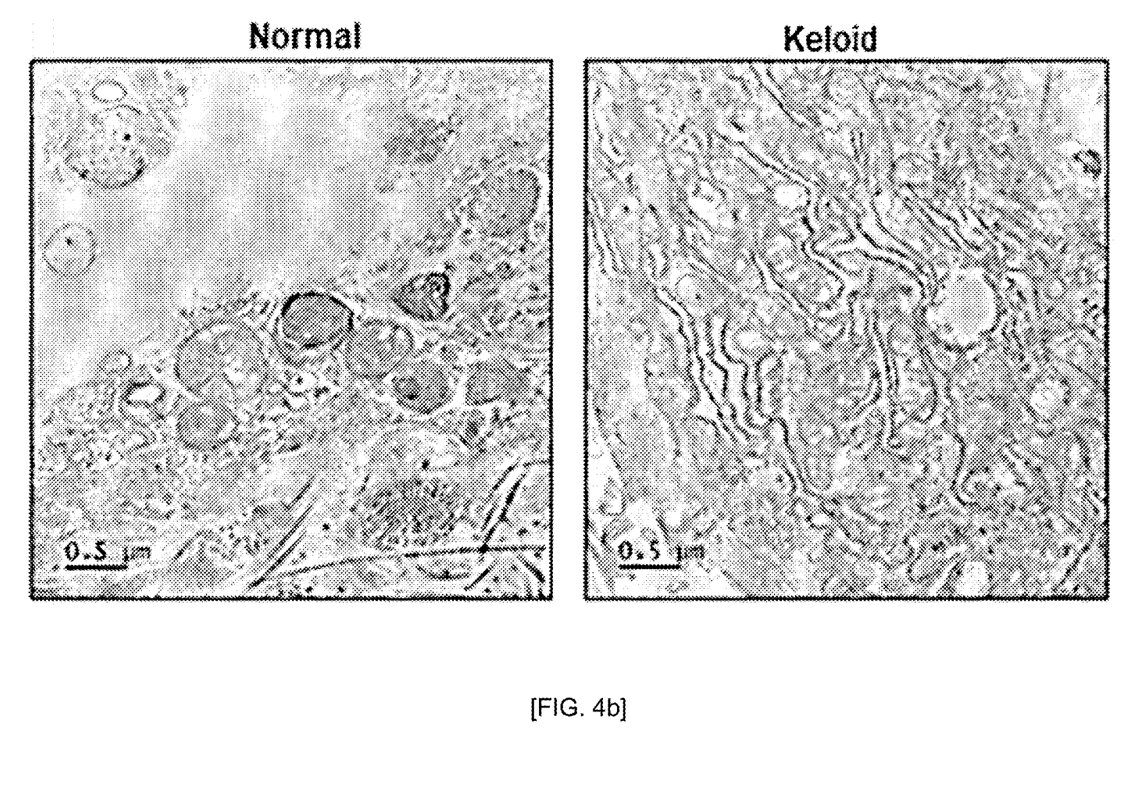

2. Increased ER Stress-Related Markers and Increased Fibrosis Marker COL1A2 in Human Keloid Tissues Compared to Normal Human Tissues As a result of observation using Western blot analysis in human keloid tissue compared to normal human tissue, ATF4, CHOP, phospho-ERK (P-ERK) and phospho-IRE1α (P-IRE1α) related to ER stress were significantly increased, and significant increases in IL-1beta, an inflammatory marker, and COL1A2 and TGFβ1 representing fibrosis were observed. As a result of observation with an electron microscope, in human keloid tissue, it was possible to observe that the ER stress was an important result in the pathogenesis of keloid by observing a significantly increased ER interval compared to normal skin tissue (FIG. 4A-4B).

Figure 5A:
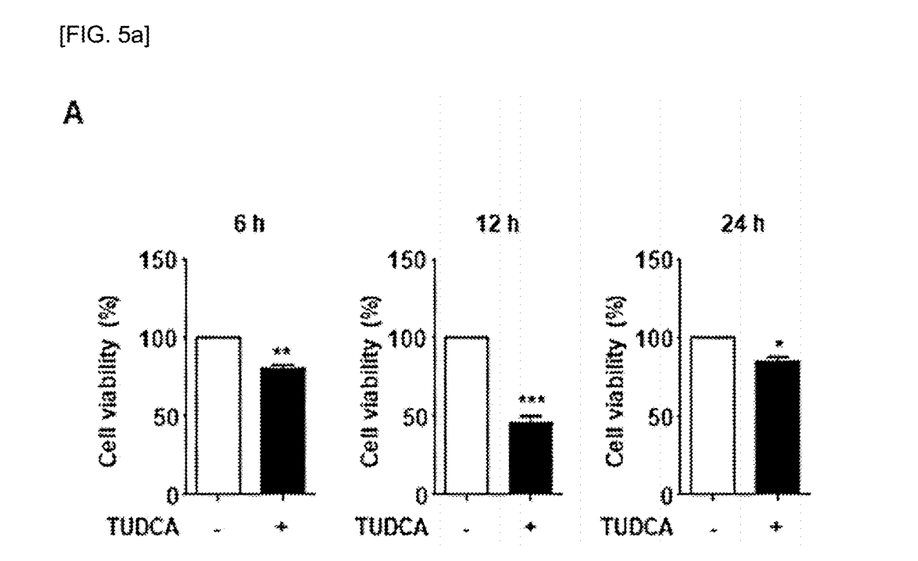
FIG. 5A-5D shows the effect of tauroursodeoxycholic acid on human keloid tissue or normal tissue-derived fibroblasts.
Figure 5B:
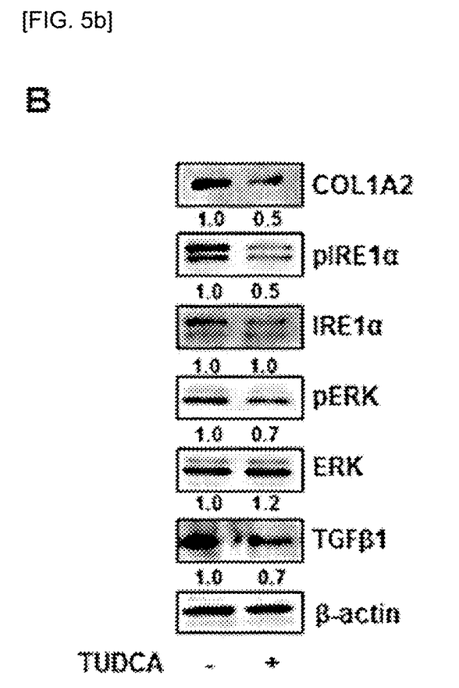
Figure 5C:
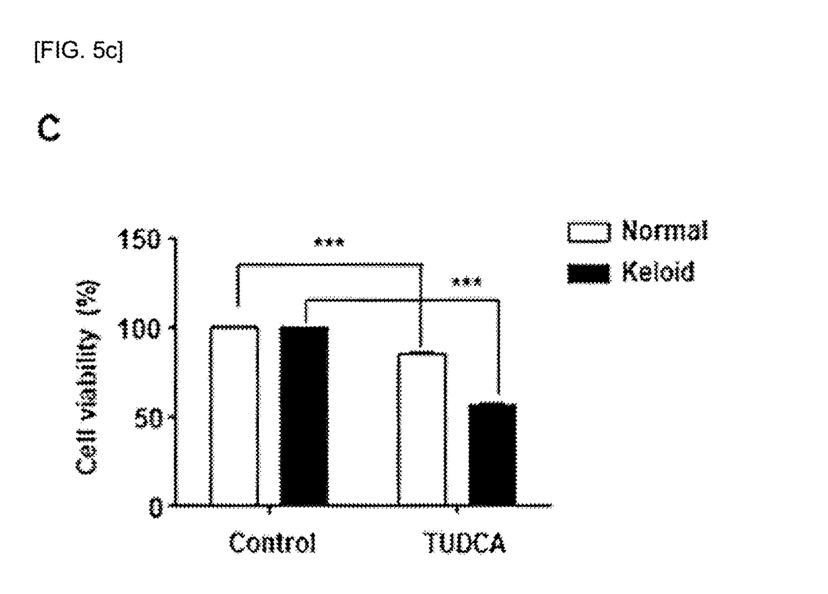
Figure 5D:
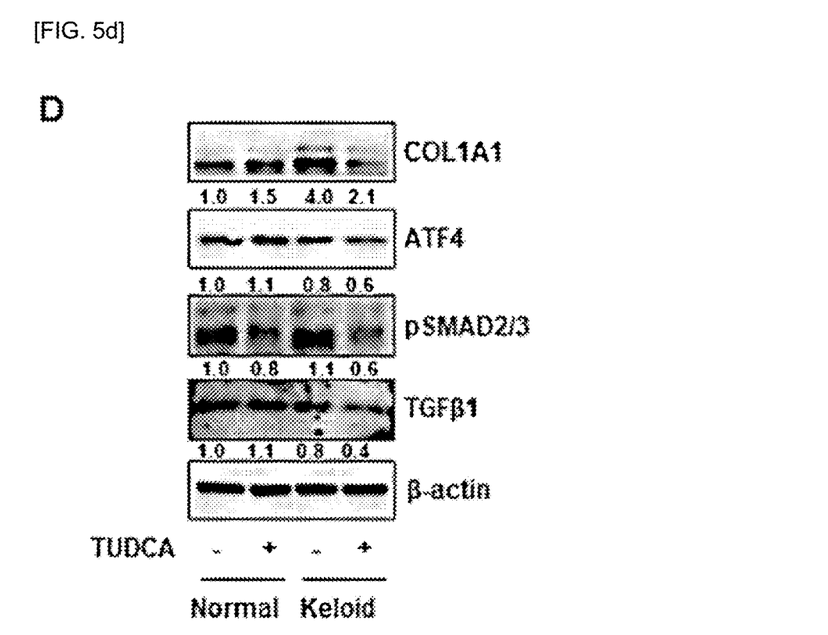

3. Efficacy of TUDCA, an ER Stress Inhibitor, and Changes in Related Markers Increased in Human Keloid Tissue-Derived Fibroblasts than in Normal Skin Tissue-Derived Fibroblasts After treatment with TUDCA, the viability of human keloid tissue-derived fibroblasts and normal skin tissue-derived fibroblasts was evaluated. In human keloid tissue-derived fibroblasts, cell viability was significantly decreased after 6 hours, 12 hours, and 24 hours after TUDCA treatment (FIG. 5A). Also, COL1A2 and ER stress-related gene expression levels were significantly reduced in TUDCA-treated human keloid tissue-derived fibroblasts (FIG. 5B). The viability of normal skin tissue-derived fibroblasts decreased 12 hours after exposure to TUDCA, but was statistically significantly lower than that of human keloid tissue-derived fibroblasts (FIG. 5C). Western blotting showed that the levels of the keloid pathway markers p-SMAD2/3 and TGFβ1 were reduced by TUDCA, and these results also showed a significant difference in human keloid tissue-derived fibroblasts than in normal skin tissue-derived fibroblasts (FIG. 5D).

4. Efficacy of TUDCA Intralesional Injection in Animal Models of Keloids

Figure 6:
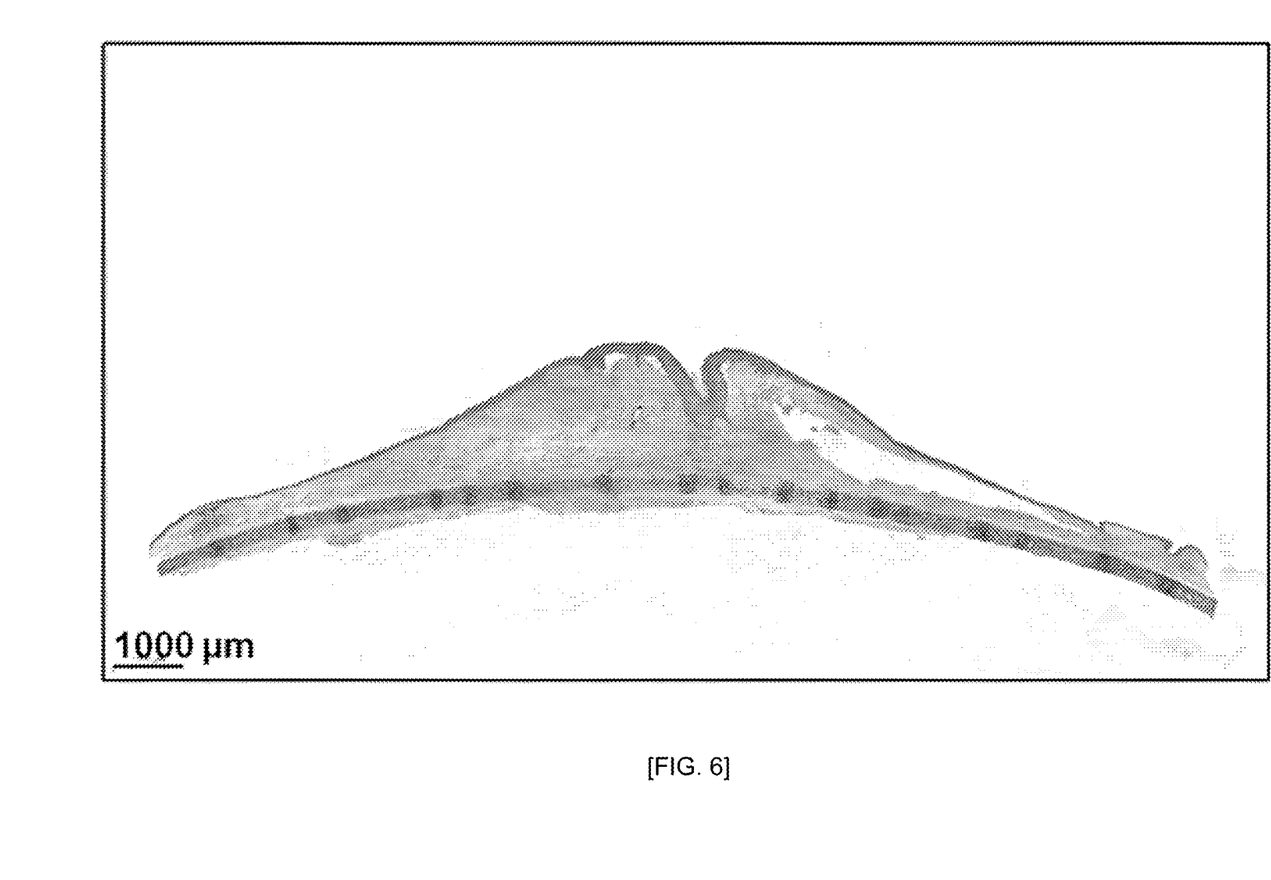
FIG. 6 shows the keloid formed in the rabbit model.

Next, the efficacy of TUDCA for keloid improvement in a rabbit ear scar model was investigated. A circular wound (10 mm in diameter) was created on the rabbit's ear, and after 20 days, a markedly raised and pigmented scar was evident, and the scar was histologically confirmed (FIG. 6).

Figure 7:
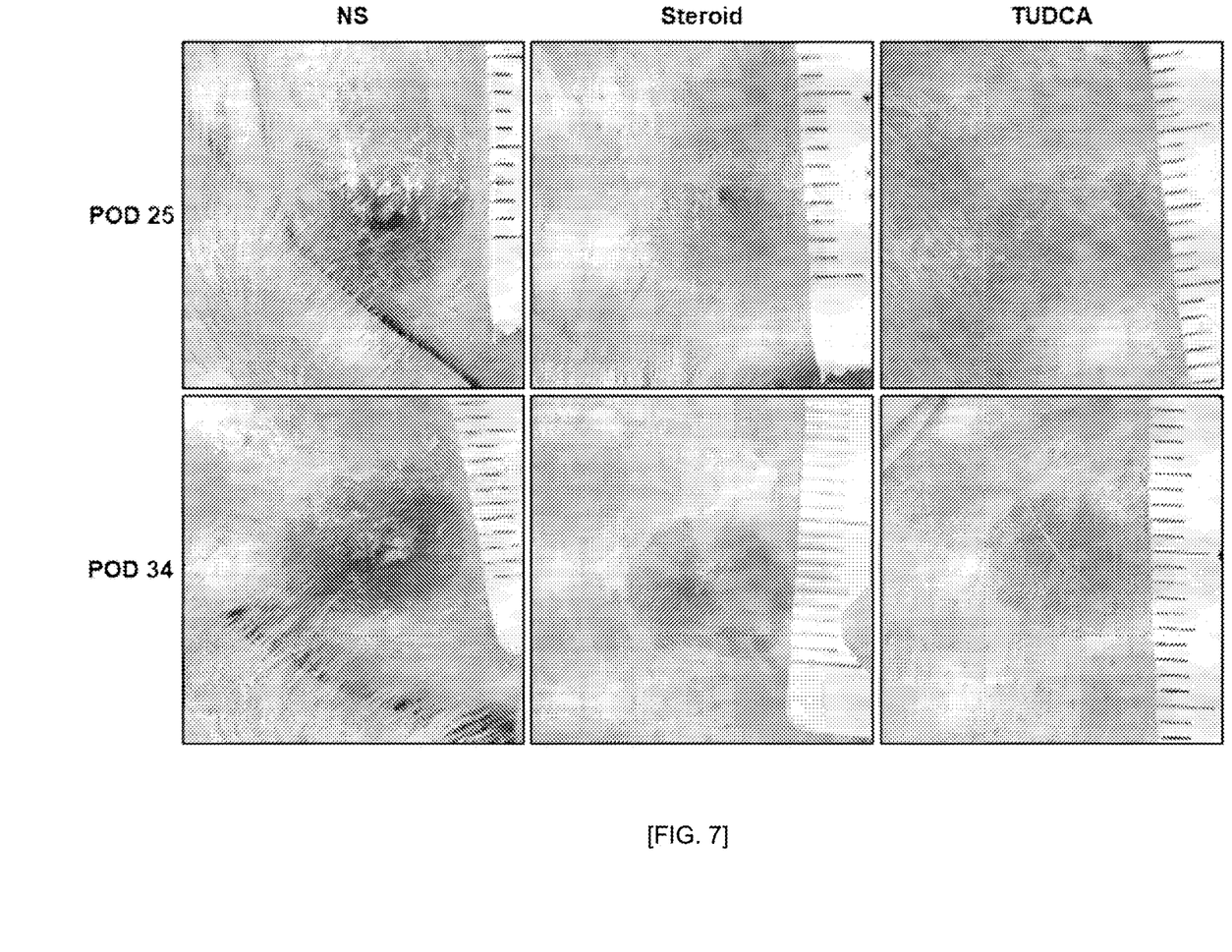
FIG. 7 shows the effect of tauroursodeoxycholic acid in an animal model of keloid.

On days 20 and 25 after wounding, normal saline (NS), steroids (10 mg/mL) or TUDCA (10 mg/mL) were injected into the scar dermis. In the saline group, the wound site consisted of palpable skin tissue similar to a hypertrophic scar with a pale red color, but in contrast, rabbit ear scars healed better after steroid or TUDCA treatment, giving a pale pink color (FIG. 7).

Figure 8:
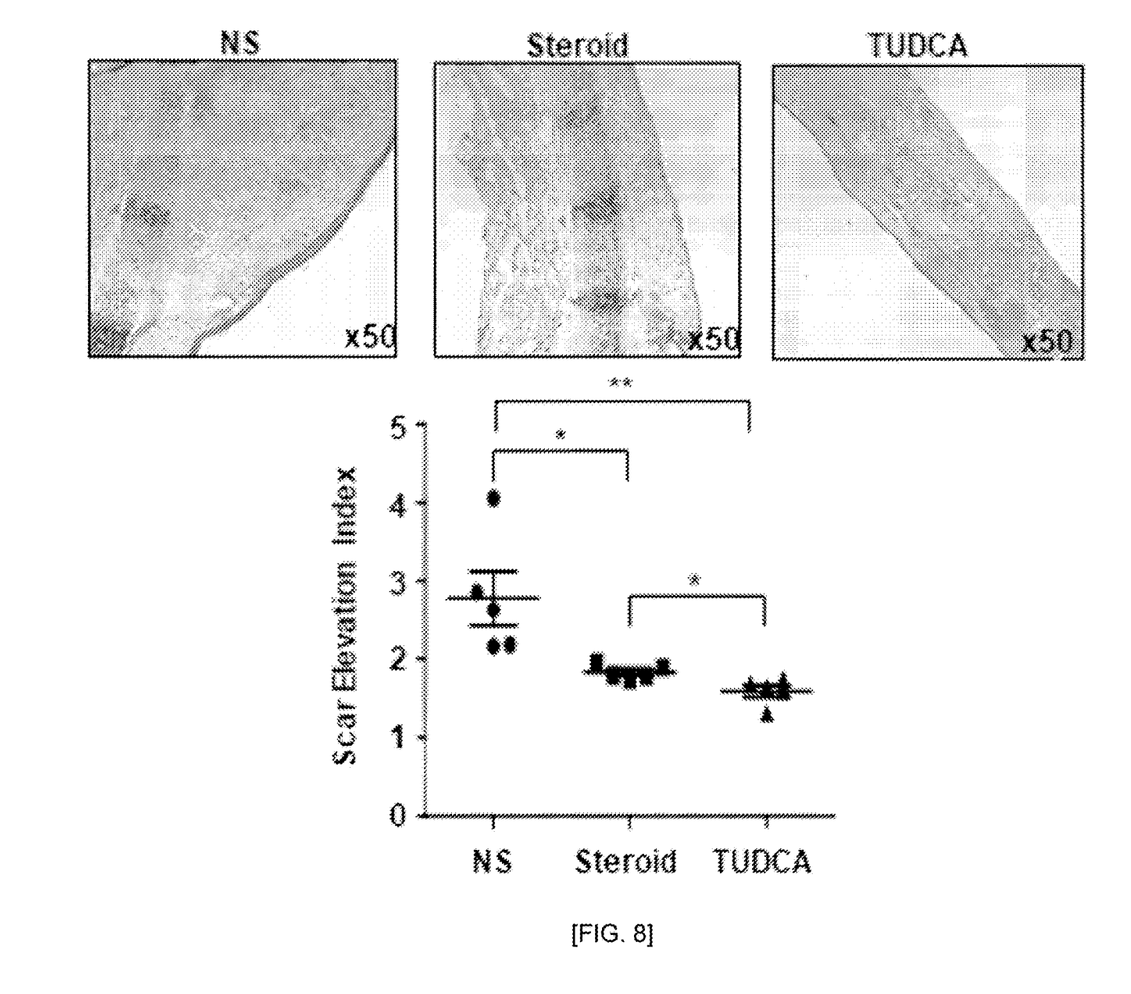
FIG. 8 shows the effect of tauroursodeoxycholic acid in an animal model of keloid.

To evaluate the effect of TUDCA and steroid treatment on scarring, the scar tissue was H&E stained and observed under a microscope. In the scar tissue of the saline group collected on the 34th day of wound induction, collagen fibers were generally thick and irregularly arranged, and inflammatory cells and fibroblasts were large and irregular. Although some irregular fiber deposition was observed in both the steroid group and the TUDCA group, the amount was significantly reduced compared to the saline group, and the scar tissue became thinner (FIG. 8). The SEI was 2.778±0.346 in the control group, 1.83±0.043 in the steroid group, and 1.586±0.074 in the TUDCA group. Both groups showed a decrease after treatment. Compared with the control group, both the steroid group ($p=0.0263$) and the TUDCA ($p=0.0098$) group showed a statistically significant decrease in SEI, and the TUDCA group showed a significantly greater decrease than the steroid group (p=0.0215). These results suggest that ER stress may be a target for keloid treatment.

What is claimed is:

1. A method for improving keloids or preventing recurrence of keloids comprising administering to a subject in need thereof a composition comprising tauroursodeoxycholic acid as active ingredient, and thereby improving keloids or preventing recurrence of keloids in the subject.

2. The method according to claim 1, wherein the composition comprising the tauroursodeoxycholic acid is injected into the dermis.

3. The method according to claim 1, comprising an additional component or method effective for the treatment of keloids or scars.

4. The method according to claim 3, wherein the additional component or method comprises at least one selected from the group consisting of an anti-inflammatory agent, an anti-fibrotic agent, a laser, and surgery.

5. The method according to claim 1, wherein the composition is in the form of an external preparation for skin or injection.

* * * * *